United States Patent [19]

Wambach et al.

[11] Patent Number: 4,780,552

[45] Date of Patent: Oct. 25, 1988

[54] PREPARATION OF FURAN BY DECARBONYLATION OF FURFURAL

[75] Inventors: Ludwig Wambach; Matthias Irgang, both of Heidelberg; Martin Fischer, Ludwigshafen, all of Fed. Rep. of Germany

[73] Assignee: BASF Aktiengesellschaft, Fed. Rep. of Germany

[21] Appl. No.: 97,070

[22] Filed: Sep. 16, 1987

[30] Foreign Application Priority Data

Sep. 23, 1986 [DE] Fed. Rep. of Germany ....... 3632255

[51] Int. Cl.$^4$ ............................................. C07D 307/36
[52] U.S. Cl. ..................................................... 549/505
[58] Field of Search ......................................... 549/505

[56] References Cited

U.S. PATENT DOCUMENTS

| | | | |
|---|---|---|---|
| 3,007,941 | 11/1961 | Copelin et al. | 549/505 |
| 3,223,714 | 12/1965 | Manly et al. | 549/505 |
| 3,257,417 | 6/1966 | Dunlop et al. | 549/505 |

FOREIGN PATENT DOCUMENTS 0096913 12/1983 European Pat. Off. .
0342857 6/1972 U.S.S.R. .

*Primary Examiner*—Richard L. Raymond
*Attorney, Agent, or Firm*—Keil & Weinkauf

[57] ABSTRACT

Furan is prepared by decarbonylation of furfural in the gas phase at elevated temperatures and under from 0.1 to 10 bar in the presence of hydrogen and a catalyst which contains platinum and/or rhodium and contains an alkali metal. The reaction is carried out in the presence of hydrogen. Catalysts which contain platinum and/or rhodium and to which cesium has been added are preferably used.

6 Claims, No Drawings

PREPARATION OF FURAN BY DECARBONYLATION OF FURFURAL

The present invention relates to a process for the preparation of furan by decarbonylation of furfural in the gas phase in the presence of hydrogen and a rhodium or platinum supported catalyst which contains an alkali metal.

It is known that furan can be prepared by passing gaseous furfural with steam over a catalyst, such as lime or a mixture of zinc chromite and manganese chromite. Processes for the decarbonylation of furfural in the presence of metal catalysts, in particular palladium, have also been disclosed. According to the literature, palladium has the highest activity, whereas rhodium, ruthenium, platinum and nickel are said to have poorer activity, for example in liquid-phase decarbonylation according to U.S. Pat. No. 3,007,941.

The catalytic decarbonylation of furfural in the gas phase or in the liquid phase is described. For the liquid-phase decarbonylation, both heterogeneous and homogeneous catalysts are known. For heterogeneous catalysis, in particular noble metal catalysts, predominantly palladium catalysts, are used. U.S. Pat. No. 3,007,941 describes palladium catalysts which are rated according to their productivity. The productivity is the yield of furan per gram of noble metal during the entire life of the catalyst. The productivity for the observed period is extrapolated to zero activity by an undisclosed method of calculation, and an extrapolated catalyst productivity is used for the evaluation. The calculated productivity is 21,000 g of furan per g of catalyst.

U.S. Pat. No. 3,257,417 describes the use of potassium acetate as a base for activating palladium catalysts for the decarbonylation of furfural in the liquid phase. Down to 10% of the initial activity, 18 kg of furan per g of palladium are prepared.

U.S. Pat. No. 2,223,714 describes the use of palladium catalysts which are activated with alkali bases having a pH above 11.

USSR Pat. No. 342,857 describes the preparation of silvan by catalytic decarbonylation of methylfurfural in the presence of catalysts which contain metals of group VIII, but in particular palladium. The catalysts are promoted with alkali metals. Extrapolated productivities are about 20 kg of methylfuran per g of palladium after 1,000 hours, ie. the space-time yield is unsatisfactory.

For industrial use, it is necessary to achieve appropriately high productivity coupled with minimum catalyst lives of several weeks before the first regeneration or a catalyst change is necessary. In the conventional processes, productivity and catalyst life are unsatisfactory.

The present invention relates to a process for the preparation of furan by decarbonylation of furfural in the gas phase at from 250° to 400° C. under from 0.1 to 10 bar in the presence of hydrogen and a catalyst containing noble metals, wherein a catalyst which contains platinum and/or rhodium and contains from 0.1 to 10.0% by weight of an alkali metal is used and the molar ratio of hydrogen to furfural is brought to not less than 0.5:1 in the reaction.

Catalysts which contain platinum and/or rhodium and contain from 0.1 to 10.0% by weight of cesium are preferably used.

Surprisingly, catalysts containing platinum and rhodium exhibit substantially better productivities and lives than palladium-containing ones. Comparison of the productivities of the novel platinum and rhodium catalysts with the known palladium catalysts shows the great superiority. This is surprising because, in other processes which are carried out in the liquid phase, rhodium and platinum are attributed a poor activity (U.S. Pat. No. 3,007,941 and European Pat. No. 913).

The decarbonylation is carried out in the gas phase by a continuous procedure at from 250° to 400° C., preferably from 300° to 350° C., under from 0.1 to 10 bar, preferably under atmospheric pressure.

The process can be carried out either in a tube reactor using catalyst material in the form of pieces, or in a fluidized bed.

Platinum or rhodium supported catalysts which contain alkali metals or alkali metal compounds are used as catalysts. The noble metal content is from 0.01 to 10, preferably from 0.1 to 2,% by weight, based in each case on the total weight of the catalyst.

The content of alkali metal is from 0.1 to 10.0% by weight. Na, K and/or preferably Cs compounds are advantageously used. The salts of weak acids, ie. of acids having a dissociation constant of less than $1-10^{-3}$ are preferably used as alkali metal compounds. The alkali metals are present in the ready-prepared catalyst in general in the form of their oxides.

The catalysts are generally applied to inert and mechanically stable carriers, examples of suitable carriers being alumina, titanium dioxide, silica, aluminum silicates, zeolites, magnesium silicate and active carbon. Alumina is preferably used.

The catalyst is prepared in two stages. First, the carrier can be impregnated with the required amount of the noble metal salt solution, for example with nitrate solution, and then dried at from 70° to 200° C. and heated at from 300° to 700° C. In the second stage, the alkali metal can be applied in the form of its carbonate, acetate, hydroxide or other soluble salts. After the second impregnation process, the catalyst is generally dried at from 70° to 200° C., preferably at from 100° to 140° C. The catalyst can then be heated at from 300° to 700° C., preferably from 500° to 550° C.

The resulting catalyst is advantageously reduced with hydrogen before use. This can be done at from 150° to 500° C., preferably from 250° to 350° C. In this procedure, the hydrogen can be fed in in pure form or can be diluted, for example with nitrogen. The duration of the reduction is from 2 hours to 1 day, preferably 10 hours.

The decarbonylation is carried out in the presence of hydrogen as a carrier gas, the hydrogen also having the function of prolonging the catalyst life. The hydrogen/furfural ratio can be chosen within wide limits, a molar ratio of hydrogen to furfural of from 0.5:1 to 2:1, in particular 0.75:1, being preferred.

The advantage of the present invention is that long catalyst lives and correspondingly high productivities can be obtained in combination with a high throughput. For example, as described in the Examples below, from 40 to 80 kg of furan can be produced per g of platinum or rhodium before the activity of the catalyst has fallen to 70% conversion, the space velocity being 1.8 moles of furfural per 100 g of catalyst per hour. In Example 3, more than 130 kg of furan are produced under the same conditions. This is better than the prior art productivities by a factor of 6.

TABLE

Furan productivities of the newly developed catalysts compared with the prior art

| Catalyst | Phase | Temp. | Productivity (g of furan/g of metal) |
|---|---|---|---|
| Example 1 (0.79% of Pt, 1.65% of $Na_2O$ on $Al_2O_3$) | Gas | 300–350° C. | 80,000 to residual activity of 70% |
| Example 2 (0.75% of Pt, 2% of $Cs_2CO_3$ on $Al_2O_3$) | Gas | 300–350° C. | 131,500 to residual activity of 70% |
| Example 3 (1% of Rh, 1.5% of $Na_2O$ on $Al_2O_3$) | Gas | 300° C. | 40,000 to residual activity of 70% |
| 10% of Pd/C + $Na_2CO_3$ (U.S. Pat. No. 3,007,941) | Liquid | 200° C. | 21,000 extrapolated to residual activity of 0% |
| 5% of Pd/$Al_2O_3$ + Ca($CH_3COO$)$_2$ (U.S. Pat. No. 3,257,417) | Liquid | 215° C. | 17,690 to residual activity of 10% |
| 0.3% of Pd/$Al_2O_3$ + $Na_4SiO_4$ (U.S. Pat. No. 3,223,714) | Gas | 300° C. | 16,500 to residual activity of 10% |
| 2% of Pd/C + 2% of $Cs_2CO_3$ (USSR Pat. No. 342,857) | Gas | 240–320° C. | 20,000 g of silvan to only 80% of the initial activity |

Catalyst A 600 g of $Al_2O_3$ extrudates are impregnated with 360 ml of platinum nitrate solution (1.5% of Pt). Drying is carried out at 120° C. and heating at 520° C. Thereafter, impregnation is effected with a solution of 15 g of $Na_2CO_3$ in 360 ml of water, and the product is again dried at 120° C. and heated at 520° C. The ready-prepared catalyst contains 1.65% by weight of $Na_2O$ and 0.79% of Pt.

Catalyst B

The procedure described for catalyst A is followed, except that a solution of 27 g of $Cs_2CO_3$ in 360 ml of water is used for the second impregnation. The catalyst contains 0.75% of Pt and 4% of $Cs_2CO_3$.

Catalyst C 650 g of extrudates of gamma-$Al_2O_3$ are impregnated with 365 ml of a rhodium nitrate solution (1.8% of Rh). The resulting product is dried at 120° C., heated at 520° C. and again impregnated with a solution of 17 g of $Na_2CO_3$ in 345 ml of water. The catalyst is again dried at 120° C. and heated at 520° C., after which it contains 1.0% by weight of Rh and 1.5% by weight of $Na_2O$.

EXAMPLE 1

The reaction is carried out in a vertical, electrically heated tube reactor having an internal diameter of 35 mm and a height of 450 mm. 100 g of supported catalyst A are introduced into the tube reactor and heated to 300° C. A gas mixture of furfural and hydrogen is passed continuously over this catalyst by the cocurrent method. The feed rate is 1.8 moles of furfural per hour and 1.34 moles of hydrogen per hour. Furfural is separated off from the reaction mixture and recycled, while furan is condensed in cold traps and analyzed by gas chromatography. A small amount of methylfuran and traces of n-butanal and propene are found as by-products.

Initial conversion is 93%, but this falls steadily. After continuous operation for 510 hours, the reaction temperature is increased to 350° C. since the conversion has fallen to 70%. The temperature increase has the effect of increasing the conversion again, but this again falls to 70% after 590 hours. The feed is therefore shut off after 590 hours. Up to this point, 80 kg of furan per g of platinum are prepared, the mean selectivity being 90%.

EXAMPLE 2

The procedure described in Example 1 is followed, and a rhodium catalyst C containing 1% of Rh and 1.5% of $Na_2O$ on $Al_2O_3$ is used. The selectivity varies from 91 to 95% at a conversion of 90%, which falls to 70% after 390 hours. 40 kg of furan per g of rhodium are prepared during this time.

EXAMPLE 3

100 g of catalyst B are introduced into the tube reactor described in Example 1. The procedure described in Example 1 is followed, except that the reactor temperature is increased from 300° to 310° C. after the first 300 hours of operation. Every further 200 hours of operation, the temperature is increased by a further 10° C. The selectivity is initially 90% and increases continuously to 95% after 1,430 hours. The conversion is initially 99%. After 1,430 hours of operation, a conversion of 70% is still achieved. 131.5 kg of furan are produced during this time.

We claim:

1. A process for the preparation of furan comprising decarbonylating furfural in the gas phase at from 250° to 400° C. at a pressure of from 0.1 to 10 bar in the presence of hydrogen and a catalyst containing from 0.01 to 10% by weight of platinum, rhodium or mixture thereof and from 0.1 to 10.0% by weight of an alkali metal, the molar ratio of hydrogen to furfural being not less than 0.5:1.

2. The process of claim 1 wherein said alkali metal is cesium.

3. The process of claim 1 wherein said catalyst contains platinum.

4. The process of claim 1 wherein said catalyst contains rhodium.

5. The process of claim 1 wherein said catalyst contains platinum and rhodium.

6. The process of claim 2 wherein said catalyst contains platinum.

* * * * *